(12) United States Patent
Akahoshi et al.

(10) Patent No.: US 8,545,395 B2
(45) Date of Patent: Oct. 1, 2013

(54) ENDOSCOPICALLY INSERTING SURGICAL TOOL

(75) Inventors: Kazuya Akahoshi, Fukuoka (JP); Hidefumi Akahane, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 708 days.

(21) Appl. No.: 12/506,441

(22) Filed: Jul. 21, 2009

(65) Prior Publication Data

US 2010/0022826 A1 Jan. 28, 2010

(30) Foreign Application Priority Data

Jul. 22, 2008 (JP) ................................. 2008-188225

(51) Int. Cl.
*A61B 1/00* (2006.01)

(52) U.S. Cl.
USPC ............................ 600/104; 600/114; 600/154

(58) Field of Classification Search
USPC ................................................. 600/104, 154
See application file for complete search history.

(56) References Cited

U.S. PATENT DOCUMENTS

| | | | | |
|---|---|---|---|---|
| 4,945,920 | A * | 8/1990 | Clossick | 600/564 |
| 4,967,732 | A * | 11/1990 | Inoue | 600/139 |
| 5,066,295 | A * | 11/1991 | Kozak et al. | 606/47 |
| 5,820,546 | A | 10/1998 | Ouchi | |
| 6,015,381 | A * | 1/2000 | Ouchi | 600/104 |
| 6,113,586 | A * | 9/2000 | Ouchi | 606/1 |
| 6,235,026 | B1 * | 5/2001 | Smith | 606/46 |
| 6,443,909 | B1 * | 9/2002 | Ouchi | 600/562 |
| 6,520,954 | B2 * | 2/2003 | Ouchi | 606/1 |
| 6,605,077 | B2 * | 8/2003 | Whittier et al. | 606/1 |
| 6,890,294 | B2 * | 5/2005 | Niwa et al. | 600/106 |
| 6,972,017 | B2 * | 12/2005 | Smith et al. | 606/47 |
| 7,052,495 | B2 * | 5/2006 | Smith | 606/47 |
| 7,169,167 | B2 * | 1/2007 | Chu | 606/205 |

(Continued)

FOREIGN PATENT DOCUMENTS

| | | |
|---|---|---|
| DE | 103 56 018 A1 | 7/2004 |
| EP | 1 554 974 A1 | 7/2005 |

(Continued)

OTHER PUBLICATIONS

Office Action issued in corresponding European Application No. 09009290.9-2310.

(Continued)

*Primary Examiner* — Matthew J Kasztejna
(74) *Attorney, Agent, or Firm* — Birch, Stewart, Kolasch & Birch, LLP

(57) ABSTRACT

An endoscopically inserting surgical tool is composed of an elongated flexible cord to be passed through a tool guide channel on an endoscope, and a tool action mechanism mounted on a fore distal end of the flexible cord to be projected out of the tool guide channel. The flexible cord has such a length that, when the tool action mechanism is projected out of a tool exit opening at the end of the tool guide channel, a proximal end portion of the flexible cord still remains outside and rearward of a tool entrance way which is provided on a manipulating head grip of the endoscope as an approach to the tool guide channel. A proximal end portion of the flexible cord is gripped in a rotary tool adjustor which is manipulable to turn the tool action mechanism clockwise or counterclockwise together with the flexible cord in the tool guide channel of the endoscope.

4 Claims, 13 Drawing Sheets

(56) References Cited

U.S. PATENT DOCUMENTS

| | | | |
|---|---|---|---|
| 7,347,816 B2 * | 3/2008 | Niwa et al. | 600/154 |
| 7,727,144 B2 * | 6/2010 | Suzuki | 600/106 |
| 7,927,271 B2 * | 4/2011 | Dimitriou et al. | 600/106 |
| 2001/0004676 A1 * | 6/2001 | Ouchi | 600/106 |
| 2003/0009854 A1 | 1/2003 | Shippert | |
| 2003/0028096 A1 * | 2/2003 | Niwa et al. | 600/424 |
| 2004/0210111 A1 | 10/2004 | Okada | |
| 2004/0236214 A1 | 11/2004 | Opie et al. | |
| 2005/0182292 A1 * | 8/2005 | Suzuki | 600/104 |
| 2009/0088600 A1 * | 4/2009 | Meloul | 600/104 |

FOREIGN PATENT DOCUMENTS

| | | |
|---|---|---|
| EP | 1 808 118 A1 | 7/2007 |
| GB | 2 321 193 A | 7/1998 |
| JP | 9-299323 A | 11/1997 |
| WO | WO 2007/136894 A2 | 11/2007 |

OTHER PUBLICATIONS

Office Action dated Aug. 21, 2012 issued in Japanese Patent Application No. 2008-188225 (English translation is attached).

* cited by examiner

ENDOSCOPICALLY INSERTING SURGICAL TOOL

TECHNICAL FIELD

This invention relates to an endoscopically inserting surgical or bioptic tool having an action mechanism of the tool at a distal end of an elongated flexible cord to be placed in a tool guide channel of an endoscope.

TECHNICAL BACKGROUND

Generally, an endoscope for medical use has an elongated flexible insertion tube extended forward from a manipulating head grip for insertion into a body cavity. On the proximal side away from the flexible insertion tube, a universal connection cable is led out from the manipulating head grip for connection to peripheral units. An endoscopic observation means including an illumination window or windows and an optical observation window is provided at a fore distal end of the endoscopic insertion tube thereby to observe and examine an intracavitary site of interest. In case a lesion is spotted as a result of an endoscopic examination, it may become necessary to give a suitable treatment to the lesion or to sample a cellular specimen or specimens. For this purpose, a tool guide channel is usually provided on a medical endoscope to extend between a tool entrance way, which is provided on a manipulating head grip of the endoscope, and a tool exit opening which is provided at a fore distal end of the elongated insertion tube of the endoscope. Since the elongated insertion tube of the endoscope has to be flexible in bending directions, the tool guide channel is normally constituted by a tube which is also flexible in bending directions of the insertion tube.

Examples of bioptic or surgical tools to be introduced into a body cavity by way of a tool guide channel on an endoscope include, in addition to forceps such as bioptic forceps and grasper forceps, high frequency tools such as high frequency knife or snare, cytodiagnostic brush and shadowing agent feeder tube. In tools of this sort, a manipulation handle is attached at a proximal end of a tool, and functional action parts of the tool are mounted on a distal end of a flexible cord from the manipulating handle. The surgical or bioptic tool is placed in a tool guide channel on an endoscope through an entrance way on a manipulating head grip of the endoscope, and pushed forward to protrude out of a tool exit opening at the distal end of an elongated insertion tube of the endoscope over a certain length for necessary for giving a required treatment.

For example, in case of a high frequency tool like a high frequency knife with a rod-like electrode member or a cytodiagnostic brush, there is no need for orienting the tool to a particular radial direction upon protrusion from a tool exit opening at the distal end of the tool guide channel on the endoscopic insertion rod. However, forceps as well as shadowing agent feeder tube needs to be oriented toward a specific radial direction at the time of protrusion from the tool exit opening. More specifically, in the case of forceps having a pair of grasping jaw members operably connected to a flexible cord, it is necessary for the forceps to be correctly oriented to a radial direction facing toward a target point of treatment for performing a required function as soon as it is protruded out of a tool exit opening at the end of the tool guide channel. In this regard, from the standpoint of improving maneuverability of a surgical or bioptic tool, a functional action mechanism of a tool should be adjustable in radial directions at the time of protrusion from the tool exit opening. Similarly, a high frequency tool like a high frequency knife as well as a high frequency snare requires an adjustment to a particular radial direction depending upon the shape of the tool.

The radial orientation of functional action elements of a tool should preferably be made by remote control from a position rearward of a tool entrance way on a manipulating head grip of an endoscope. In this regard it is difficult to directly turn a flexible cord of a tool clockwise or counterclockwise from that position in such a way as to transmit a clockwise or counterclockwise rotation correctly to the action elements at the distal end of the flexible cord. The radial or angular orientation of functional action elements of a tool becomes extremely difficult especially in a case where outer surfaces of a flexible cord of a tool are left in frictional contact with inner surfaces of a tool guide channel.

In this connection, disclosed in a Japanese patent application laid open under 2005-34623 is a tool orientation mechanism in which a sheathing tube is fitted relatively rotatably around an insert tube having forceps members attached to a fore distal end of a flexible cord which is in turn connected to a manipulation member at its proximal end thereby to rotate the insert tube relative to the sheathing tube. In this case, when the manipulation member is rotated relative to the sheathing tube, its rotation can be transmitted securely to the forceps members at the distal end of the flexible cord to orient the action elements to a particular radial or angular direction.

By the way, in the case of an endoscopically inserting a bioptic or surgical tool, it is a must for the flexible cord of the tool to have a length which is sufficient enough for letting a functional action element of the tool protrude out of a tool exit opening at the end of the tool guide channel over a length necessary for performing a required function. For this purpose, it is the general practice for such a tool to have a flexible cord which is longer than the endoscopic tool guide channel in total length. In addition, in order to be adaptable to a diversity of endoscopes with insertion tubes of different sizes, generally an endoscopically inserting tool is attached with a flexible cord which is way longer than a tool guide channel on an endoscope. That is to say, a manipulation member at the proximal end of a tool is necessarily located at a distant position from a tool entrance way on a manipulating head grip of an endoscope, necessarily leaving a proximal end portion of the flexible cord freely in an open air rearward of the tool entrance way over a redundantly large length which would cause flexural deformations to the flexible cord to such a degree as to make it difficult for an operator or nursing staff to orient the tool to an aimed or intended direction by way of the manipulation member at the proximal end of the flexible cord.

SUMMARY OF THE INVENTION

In view of the foregoing situations, it is an object of the present invention to provide an endoscopically inserting tool with a rotary tool adjustor capable of transmitting rotation securely to a fore distal end of the tool which is placed in a tool guide channel of an endoscope, from a position outside of a tool entrance way on a manipulating head grip of the endoscope.

It is another object of the invention to provide an endoscopically inserting surgical tool with a rotary tool adjustor allowing an operator or an assistant operator to turn a tool action mechanism at the distal end of a flexible cord of the tool clockwise or counterclockwise easily from a position in the vicinity of a manipulating head grip of an endoscope.

According to the present invention, in order to achieve the above-stated objectives, there is provided an endoscopically inserting surgical tool having an action mechanism of the tool mounted at a distal end of a flexible cord to be placed in a tool guide channel of an endoscope through a tool entrance way on a manipulating head grip of the endoscope and projected out of a tool exit opening at a distal end of the tool guide channel, the action mechanism being actuated by way of a manipulation handle connected to a proximal end portion of the flexible cord, characterized in that: the flexible cord has a length such that a proximal end portion thereof remains outside and rearward of the tool entrance way to the tool guide channel when a fore distal end portion is projected out of the tool exit opening of the tool guide channel over a necessary length for performing a required function; the proximal end portion of the flexible cord being gripped in a rotary tool adjustor adapted to turn the flexible cord clockwise or counterclockwise within the tool guide channel to adjust the action mechanism of the tool into an aimed radial direction.

Because of directionality of function, the action mechanism of the tool, which has been placed in and projected out of a tool guide channel of an endoscope, needs to be adjusted in a radial direction to bring the action mechanism of the tool to a position facing toward an aimed point for treatment. This adjustment is made from a position immediately on the proximal side of the tool entrance way on the manipulating head grip of the endoscope. If the rotary tool adjustor were attached on a flexible cord portion which is disposed in a free state at a position distant from the tool entrance way, it would be difficult to transmit a rotational force accurately to the action mechanism at the fore distal end of the flexible cord. Therefore, the rotary tool adjustor should be attached to the flexible cord at a position in the proximity of the tool entrance way on the manipulating head grip to suppress flexures of the flexible cord between the rotary tool adjustor and the tool entrance way.

An attempt to turn a flexible cord of a tool directly with fingers would result in a failure in accurately transmitting a rotational force to an action mechanism of the tool because of difficulties of rotating the flexible cord itself. A rotational force can be transmitted to the distal end of the flexible cord in a case where an insertion tube is rotated within a sheathing tube from a position in the vicinity of a tool manipulator as in the prior art patent literature mentioned hereinbefore. However, as explained above, since the tool manipulator is located at a remote position from a tool entrance way on a manipulating head grip of an endoscope, one usually feels difficulties of manipulation in bringing a tool accurately and smoothly to a desired radial or angular position, in addition to the problems of a dual flexible tube which is complicated in construction and thicker in diameter.

Gathering from the foregoing situations, according to the present invention, the manipulability of a flexible cord in rotating an endoscopically inserted tool is improved significantly by the use of a rotary tool adjustor which is adapted to grip a proximal end portion of a flexible tube in such a way as to prohibit relative rotations therebetween and which is manipulable by way of a grip portion or portions provided on the outer peripheral side of a tubular outer shell with a far larger outside diameter as compared with the flexible tube. The grip portions of the rotary tool adjustor may be provided integrally with the outer shell or fixed on the latter by the use of a suitable fixation means. For example, the grip portion of the rotary tool adjustor can be realized by forming a number of longitudinal protuberances at intervals around the outer periphery of the outer shell or by providing a radially projecting lever or finger hook rings on the outer periphery of the outer shell.

The rotary tool adjustor may be provided fixedly on a proximal end portion of a flexible cord. However, it is more desirable for the rotary tool adjustor to be releasably fixed on a flexible cord to permit adjustments of its position in the longitudinal direction of the flexible cord. When the rotary tool adjustor is adjustable in the longitudinal direction of the flexible cord, it can be located in such a position as to optimize the axial position of the action mechanism at the distal end of the flexible cord and to suppress flexures of the flexible cord as well.

When the rotary tool adjustor is turned clockwise or counterclockwise, a flexible cord to which the rotary tool adjustor is connected should be turned, exactly following the rotation of the rotary tool adjustor. In case the rotary tool adjustor is fixed on the flexible cord by the use of an adhesive, for example, there is no possibility of relative rotations occurring between the fixed parts. However, in case the rotary tool adjustor is connected to the flexible cord adjustably in the longitudinal direction, the two parts should be connected in such a way as to preclude possibilities of relative rotations therebetween. In this regard, according to the invention, relative rotations between the rotary tool adjustor and a flexible cord are prevented by frictional force. Namely, in connecting the rotary tool adjustor to a flexible cord, the rotary tool adjustor is pressed against the latter to generate a frictional force which is large enough for preventing relative rotations therebetween.

In a case where a flexible cord is in the form of a hollow tube, the rotary tool adjustor should be arranged to apply a pressure on a flexible cord in a crush-free state. As a mechanism for preventing relative rotations of the rotary tool adjustor and flexible cord, for example, there may be employed a stop screw, a clamp member or a fastening member. A manipulative grip portion may be provided integrally with a tubular shell member of the rotary tool adjustor. Alternatively, a separately formed grip portion may be attached on the outer periphery of a tubular shell member. In case the rotary tool adjustor is composed of two parts, for example, one part can be allotted with a function of preventing relative rotations of a flexible cord, while the other member can be configured to serve as a manipulative grip portion. More particularly, the rotary tool adjustor can be composed of a tubular outer shell internally defining an axial bore for threading a flexible cord of an endoscopically inserting tool, and a clamp tube having a plural number of split clamp fingers to be brought into and out of pressed engagement with the flexible cord. The axial bore in the outer shell is tapered off in diameter in such a way that its diameter is gradually reduced toward a fore distal end. The split clamp fingers of the clamp tube are tapered off on the outer side in conformity with the shape of the tapered axial bore in the outer shell. On the inner side, preferably the clamp fingers are formed in an arcuate shape snugly fitting on the flexible cord to grip the latter with a greater frictional force.

Forceps are typical of surgical tools which have directionality in action, particularly in radial direction. Normally, a forceps is composed of a pair of grasper jaw members, which are pivotally supported at one end so that the other ends of the grasper jaw members are opened and closed toward and away from each other for a grasping action. A grasper jaw assembly is attached to a flexible cord having a manipulation wire threaded internally of a flexible sleeve, manually pushing and pulling the manipulation wire to open and close the grasping jaw members by remote control. In so doing, it becomes necessary to orient the forceps in a radial direction for opening and closing the grasping jaw members toward a target of treatment.

The above and other objects, features and advantages of the invention will become apparent from the following particular description of the invention, taken in conjunction with the accompanying drawings which show by of example some preferred embodiments of the invention. Needles to say, the present invention should not be construed as being limited to particular forms shown in the drawings.

DESCRIPTION OF PREFERRED EMBODIMENTS

Figure 1:
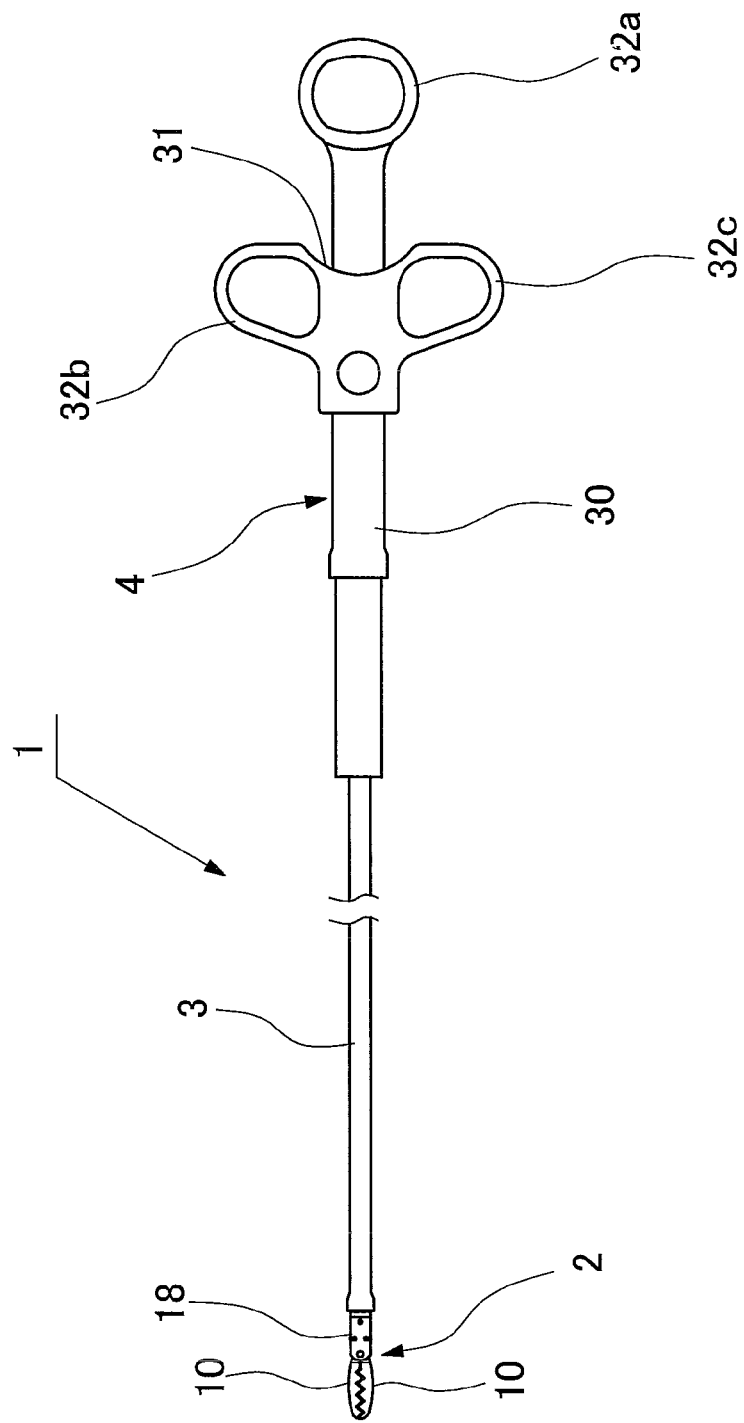
FIG. 1 is a schematic front view of a forceps, adopted as an example of endoscopically inserting surgical tools in an embodiment of the present invention.
Figure 4:
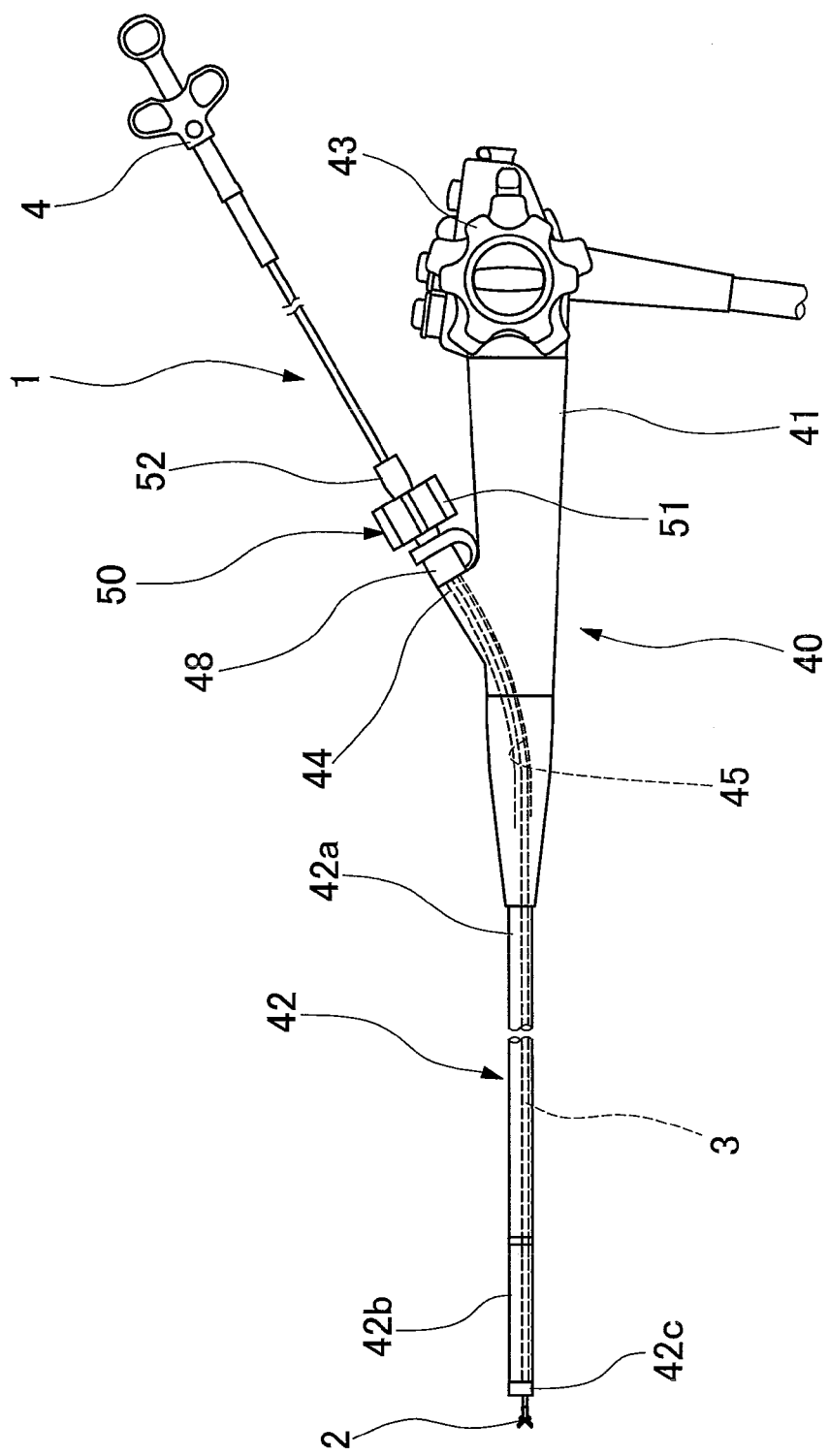
FIG. 4 is a front view of the forceps of FIG. 1, placed in a tool guide channel on an endoscope.

Hereafter, with reference to the accompanying drawings, the present invention is described more particularly by way of its preferred embodiments Here, the present invention is applied to forceps, taken as an example of an endoscopically inserting tool which needs to be orientated into a particular radial direction prior to performing a required action. Needless to say, the invention can be similarly applied to other endoscopically inserting surgical or bioptic tools. FIG. 1 shows general layout of a forceps 1 embodying the present invention, while FIG. 4 shows the forceps 1 which is placed in a tool guide channel of an endoscope 40.

Figure 2:
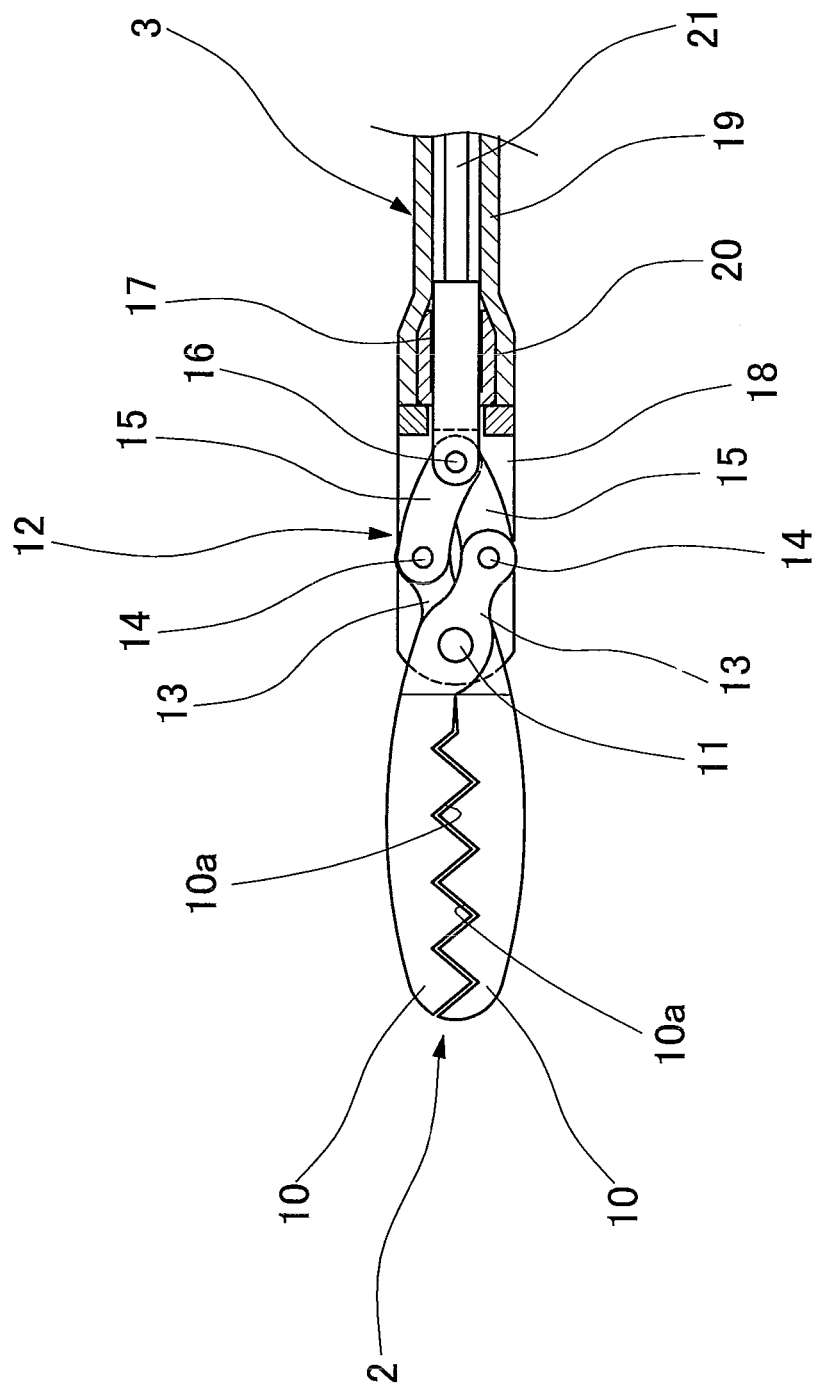
FIG. 2 is a schematic sectional view of a joint portion between the forceps of FIG. 1 and a flexible cord of the tool, showing the forceps in a closed state.
Figure 3:
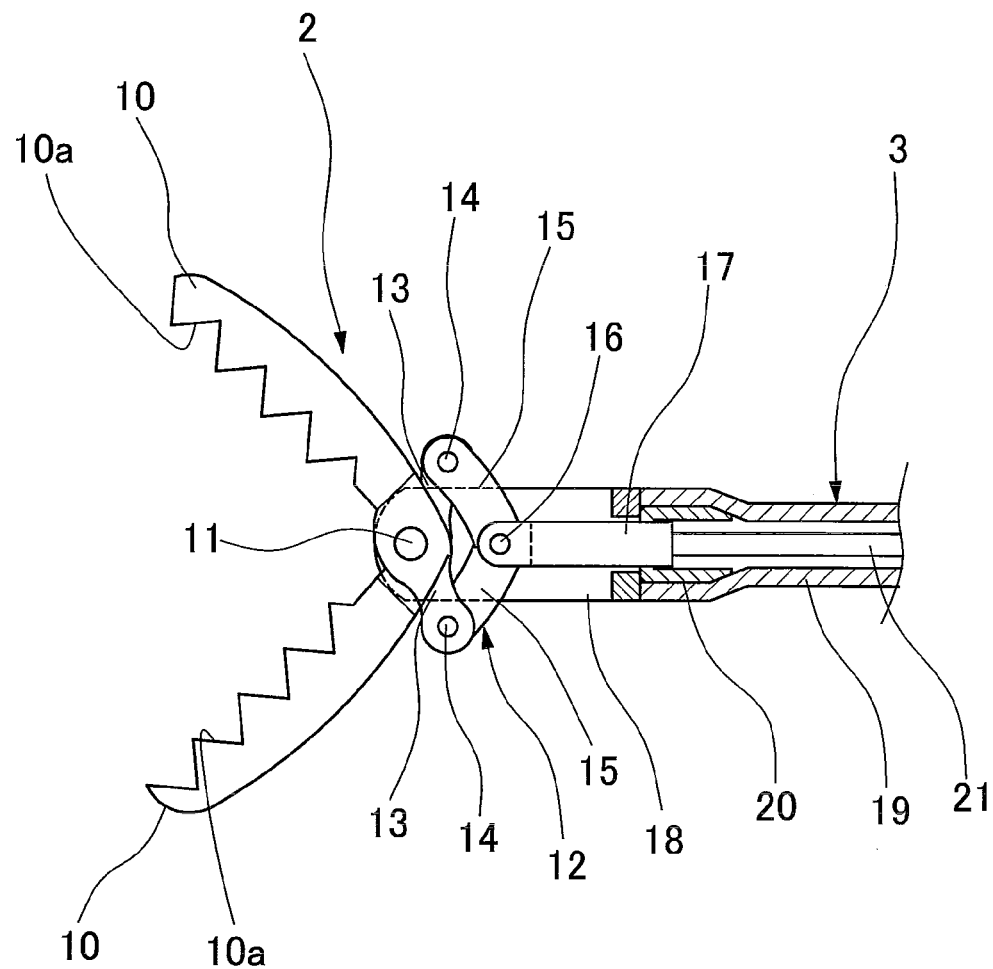
FIG. 3 is a schematic sectional view similar to FIG. 2, but showing the forceps in an opened state.

In FIG. 1, indicated at 1 is a forceps which is provided with a grasper assembly 2 at its fore distal end as an action mechanism. The grasper assembly 2 is connected to a fore distal end of a flexible cord 3 which is in turn connected to a manipulation handle 4 at its proximal end. The grasper assembly 2 and flexible cord 3 are connected with each other through a linkage mechanism as shown in FIGS. 2 and 3. The grasper assembly 2 is shown in a closed state in FIG. 2 and in an opened state in FIG. 3. The grasper assembly 2 is composed of a pair of upper and lower grasping jaw members 10 which are each formed with a series of sharp-pointed saw tooth-like gripping projections 10a on the inner meeting side. Thus, the forceps 2 is capable of gripping internal body tissues between the saw tooth-like gripping projections 10a on the upper and lower grasping jaw members 10. In order to let the forceps 2 grasp internal body tissues securely, the saw tooth-like projections 10a are preferred to be formed fully across the width of each grasping jaw member 10.

The upper and lower grasping jaw members 10 are pivotally supported on a pivotal support pin 11 so that they can be swung about the pivotal support pin 11 toward and away from each other at the time of opening and closing the grasper assembly 2. The grasping jaw members 10 are connected to a link mechanism 12 thereby to put the grasper assembly 2 in an opening or closing action. The link mechanism 12 is composed of a pair of link plates 13 which are respectively provided contiguously at posterior ends of the grasping jaw members 10 and extended rearward of the pivotal pin 11, and a pair of link plates 15 which are pivotally connected to the link plates 13 respectively through pivotal connection pins 14. Both of the link plates 15 are connected to an actuator member 17 through a pivotal connection pin 16. Thus, when the actuator member 17 is in a receded position, the jaw members 10 are held in a closed position as shown in FIG. 2. As soon as the actuator member 17 is pushed forward toward an advanced position, the jaw members 10 of the grasper assembly 2 are swung open as shown in FIG. 3.

The pivotal support pin 11 is fixed on a mount plate 18 to which a fore distal end of the flexible cord 3 is securely connected. The flexible cord 3 is provided with a flexible sleeve 19, and a connection member 20 which is securely fitted in a fore end portion of the flexible sleeve 19. The connection member 19 is fixedly connected to the mount plate 18 on the side of the grasper assembly 2 or formed integrally with the mount plate 18. The actuator member 17 is extended internally of the connection member 20 in a fore end portion of the flexible sleeve 19. A fore end of a manipulation wire 21 which is threaded through the flexible sleeve 19 is connected to the actuator member 17. In order to open and close the forceps 2, the flexible cord 3 is constituted by the combination of the flexible sleeve 19 and the manipulation wire 21 which is threaded internally of the flexible sleeve 19. However, depending upon the type of an endoscopically inserting tool, the flexible cord 3 may not be necessarily required to include the manipulation wire 21. Alternatively, the flexible sleeve 19 of the flexible cord 3 may be replaced by a tightly wound coil tube if desired.

The manipulation wire 21 is extended into the manipulation handle 4 at the rear end of the flexible cord 3. A slider member 31 with finger hooker rings 32b and 32C is slidably fitted on a shank portion 30 of the manipulation handle 4, which is provided with a finger hooker ring 32a at its proximal end. The slider member 31 is coupled with the shank portion 30 of the manipulation handle 4 by way of an axial slit which is formed on the shank portion 30. Accordingly, by pulling a thumb in the finger hooker ring 32a at the rear end of the shank portion 30 toward or away from index and middle fingers in the finger hooker rings 30b and 32c on the slider 31, the slider 31 is put in a sliding displacement toward the finger hooker ring 32a at the rear end of the shank portion 30 or in a reverse direction toward the fore end of the shank portion 30. By this sliding action of the slider 31, the manipulation wire 21 which is connected with the slider 31 is pulled in a rearward or forward direction within the flexible sleeve 19. As a result, the actuator member 17 is put in an axial displacement in a rearward or forward direction to open or close the grasping jaw members 10 of the forceps 2 through the link mechanism 12.

As shown in FIG. 4, the forceps 1 of the above-described construction is introduced into a body cavity by way of the tool guide channel on the endoscope 40. The endoscopic insertion tube 42 which is extended out from the manipulating head grip 41 of the endoscope 40 is mostly occupied by an elongated flexible tube section 42a, which is freely bendable along tortuous passage of insertion. The flexible tube section 42a is followed by relatively short articular section 42b which can be turned to a desired direction by a flexion control knob 43 which is provided on the manipulating head grip 41, and a rigid tip end section 42c, that is, a foremost section of the endoscopic insertion tube 42.

Figure 5:
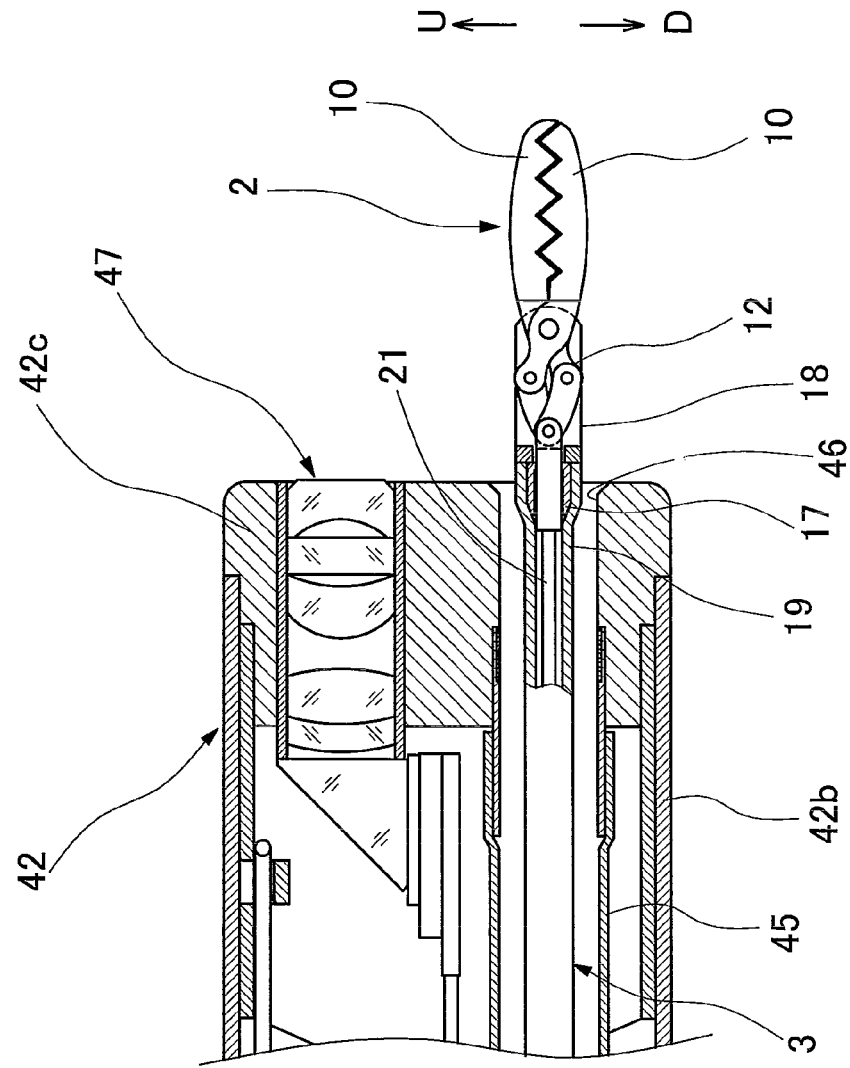
FIG. 5 is an enlarged sectional view of a fore end portion of an endoscopic insertion tube having the forceps of FIG. 4 placed in its tool guide channel.

The endoscope 40 is provided with a tool entrance way 44 on the manipulating head grip 42 as an approach to a tool guide channel 45 which is provided internally of the endoscope 40 as a tool delivery channel extending from the manipulating head grip 41 through the flexible insertion tube 42 as far as a fore distal end of the rigid tip end section 42c. Further, as shown in FIG. 5, a tool exit opening 46 is provided at the fore distal end face of the rigid tip end section to let a surgical or bioptic tool in the above-mentioned tool guide channel 45 protrude into a body cavity from the tool exit opening 46. This tool exit opening 46 is located in the vicinity of an optical endoscopic observation window 47. In addition to the endoscopic observation window 47, although not shown in the drawings, an illumination light window or windows are provided on the fore distal end face of the rigid tip end section 42c.

The insertion tube 42 of the endoscope 40 is constructed to operate on the basis of predetermined directionality, namely, to operate in upward and downward directions indicated by arrows U and D in FIG. 5, in addition to rightward and leftward directions perpendicularly to the face FIG. 5. The articular section 42b of the insertion tube 42 can be flexed in upward, downward, rightward and leftward directions by manipulation of the flexion control knob 43. Thus, the forceps 1 in the tool guide channel 45 should be appropriately oriented in a radial or clockwise or counterclockwise direction all the time when projected out of the tool exit opening 46 at the end of the tool guide channel 45. A plug or stopcock 48 is fitted in the tool entrance way 44 as a hermetical closure means.

Figure 6:
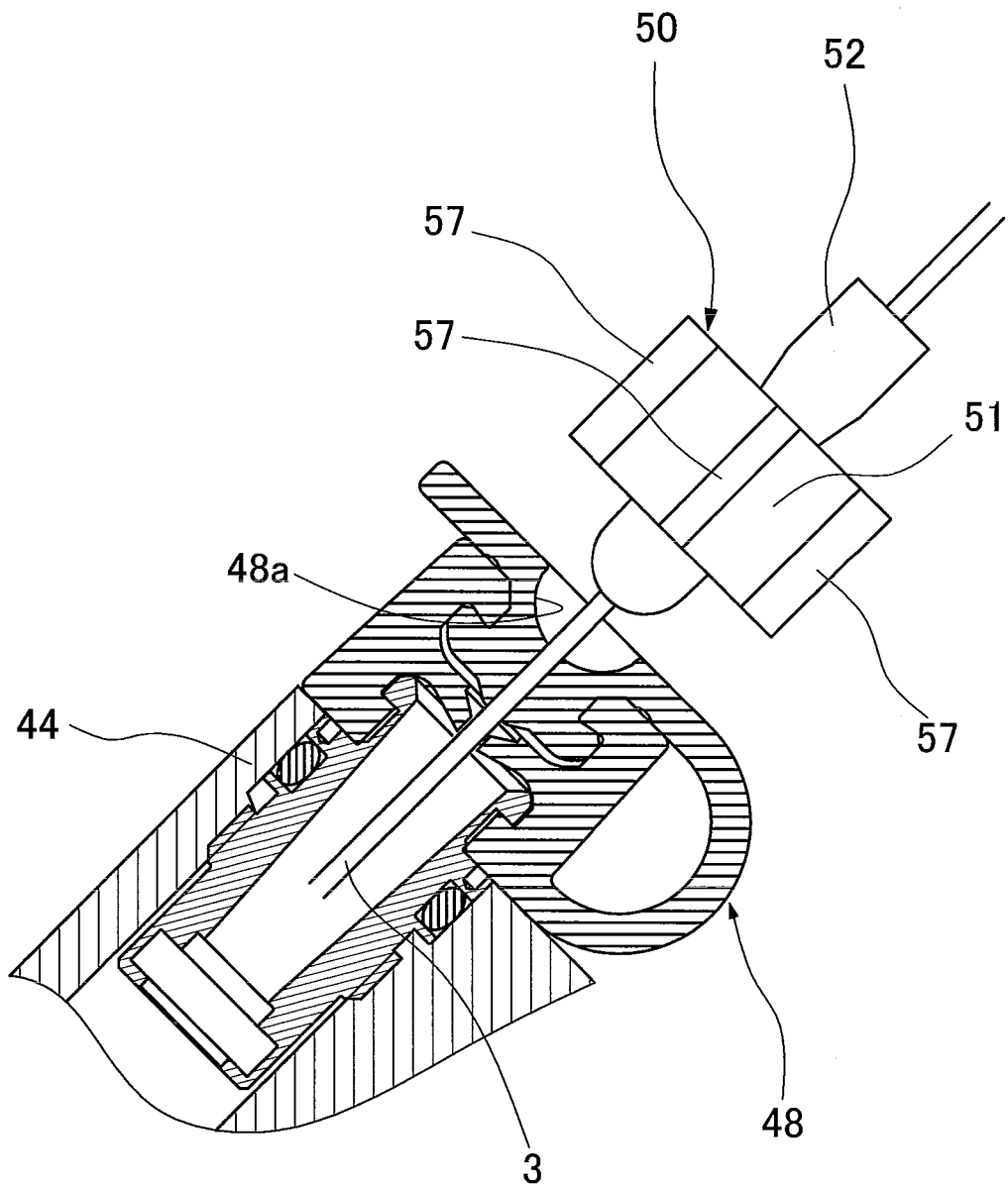
FIG. 6 is an enlarged view of an entrance way which is provided on a manipulating head grip of the endoscope as an approach to the tool guide channel.

However, when the forceps 1, placed in the tool guide channel 45 through the tool entrance way 44 on the manipulating head grip 41, is projected out through the tool exit opening 46 at the end of the tool guide channel 45, it is not necessarily oriented in a particular radial or clockwise angular direction. Therefore, the grasper assembly 2 of the forceps 1 is adjusted to take a radial position facing toward a target point within a body cavity. For this purpose, as shown in FIG. 6, a rotary tool adjustor 50 is fitted on the flexible sleeve 19 of the flexible cord 3.

Figure 7:
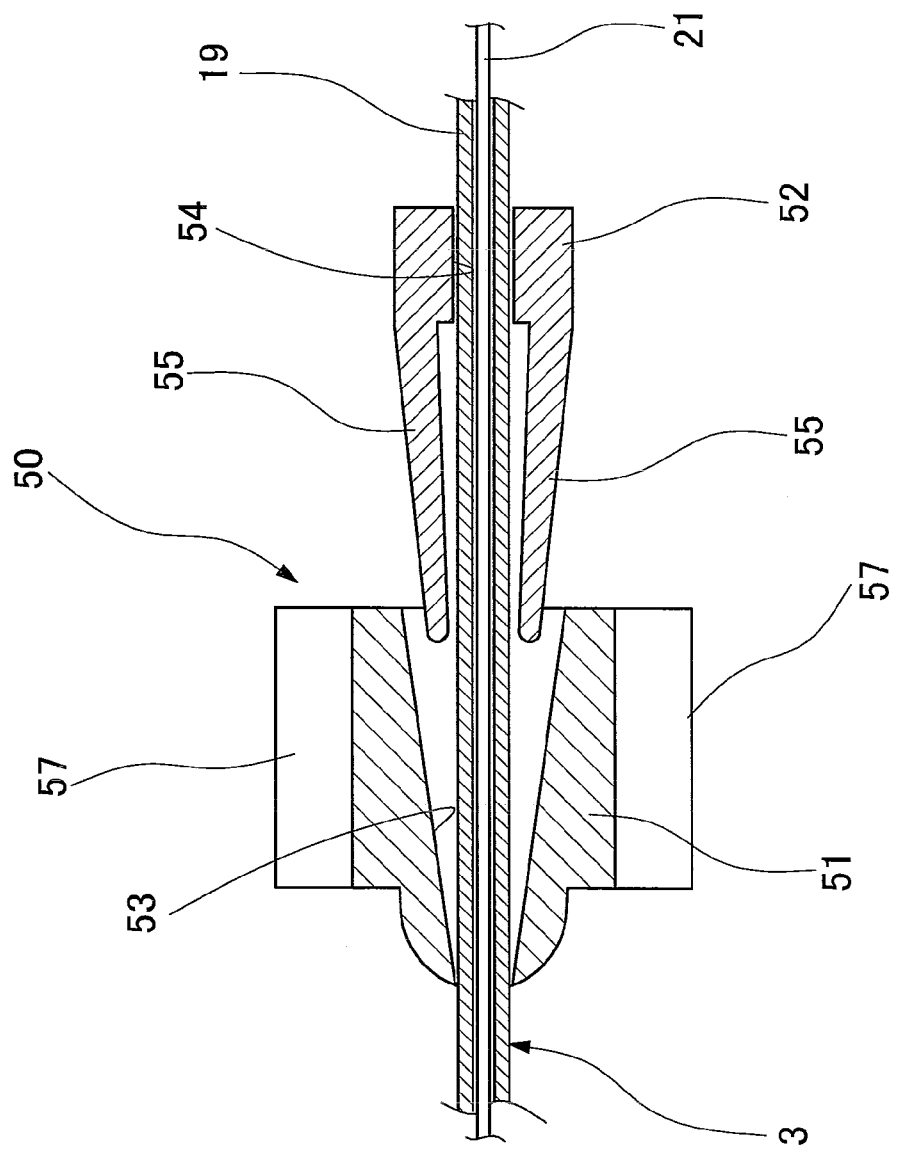
FIG. 7 is a sectional view of a rotary tool adjustor having a flexible cord threaded therethrough, showing an outer shell and an inner clamp tube in an uncoupled state.
Figure 8:
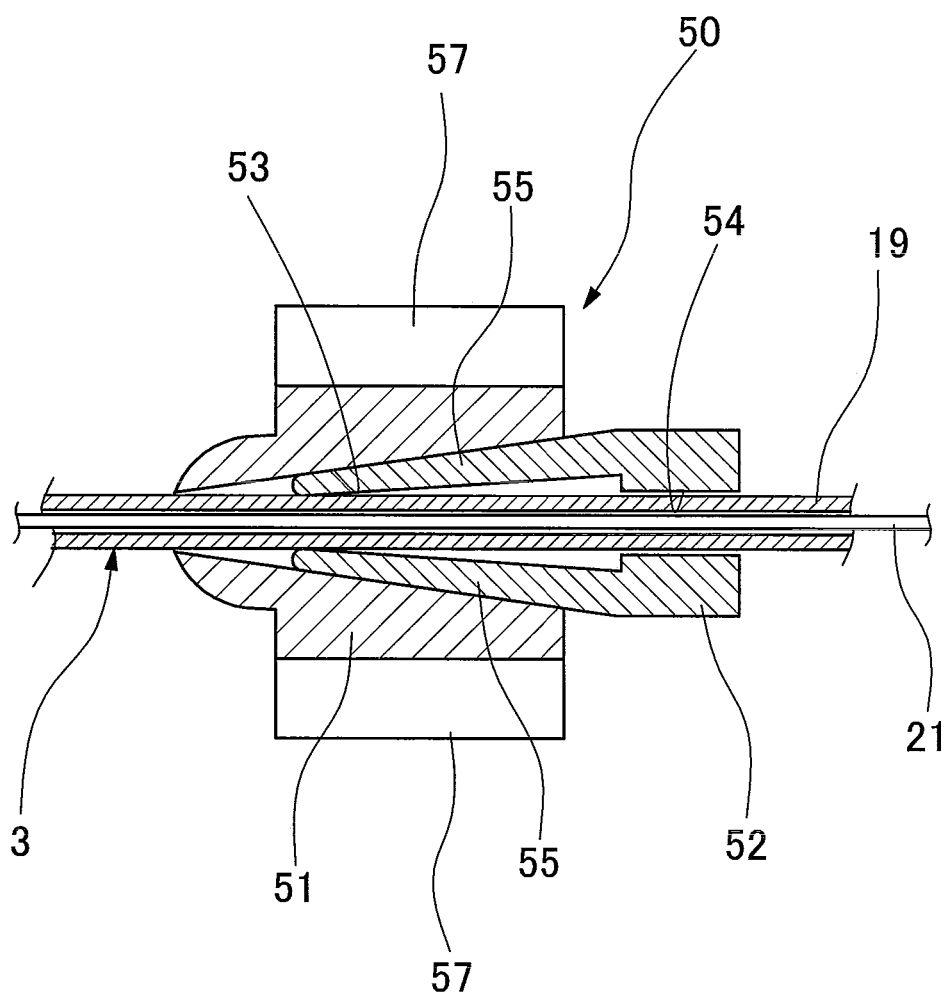
FIG. 8 is a sectional view similar to FIG. 7 but showing the outer shell and the inner clamp tube in a coupled state.

As shown in FIGS. 7 and 8, the rotary tool adjustor 50 is composed of a tubular outer shell 51 and a clamp tube 52 to be fitted in the tubular shell 51. The outer shell 51 is centrally provided with a tapered axial hole 53 which is gradually tapered off in diameter from rear to fore end. On the other hand, the clamp tube 52 is internally provided with an axial cord threading bore 54, and, as shown particularly in FIG. 9, wedge-like clamper fingers 55 to be forcibly fitted in the tapered center hole 53 of the tubular shell 51 from the rear side of the shell 51. The clamper fingers 55 are split and separated from each other by longitudinal slots 56 of a predetermined width. The separation slots 56 are narrowed down through resilient deformation when fore ends of the clamper fingers 55 are pressed toward each other from opposite sides in the tapered hole 51 of the outer shell 51.

At the time of threading the sleeve 19 of the flexible cord 3 through the tapered center hole 53 of the tubular outer shell 51 and the axial hole 54 of the clamp tube 52, the outer shell 51 and the clamp tube 52 are freely movable relative to each other while they are disengaged from each other as shown in FIG. 7. When the clamp tube 52 is put into the tapered center hole 53 of the tubular shell 51 from the wider rear end, pushing the clamper fingers 55 of the clamp tube 52 inward toward a narrower fore end of the tapered center hole 53 of the tubular shell 51 as shown in FIG. 8, the clamper fingers 55 are pressed toward each other to grip the flexible sleeve 19 securely therebetween. At the same time, the clamper tube 52 is fixed relative to the tubular shell 51 by frictional force. In this regard, a greater frictional force can be applied on the flexible cord 3 when the inner side of each clamper finger 55 is formed in an arcuate shape having substantially the same curvature as the outer contour of the flexible cord 3. After coupling the tubular shell 51 and clamp tube 52 fixedly with each other in the manner as described above, the rotary tool adjustor 50 is turned clockwise or counterclockwise to adjust the tool to a desired radial position. At this time, the flexible cord is turned along with the rotary tool adjustor 50 since the clamper fingers 55 of the rotary tool adjustor 50 function to prevent relative rotations of the sleeve 19 of the flexible cord 3.

Figure 9:
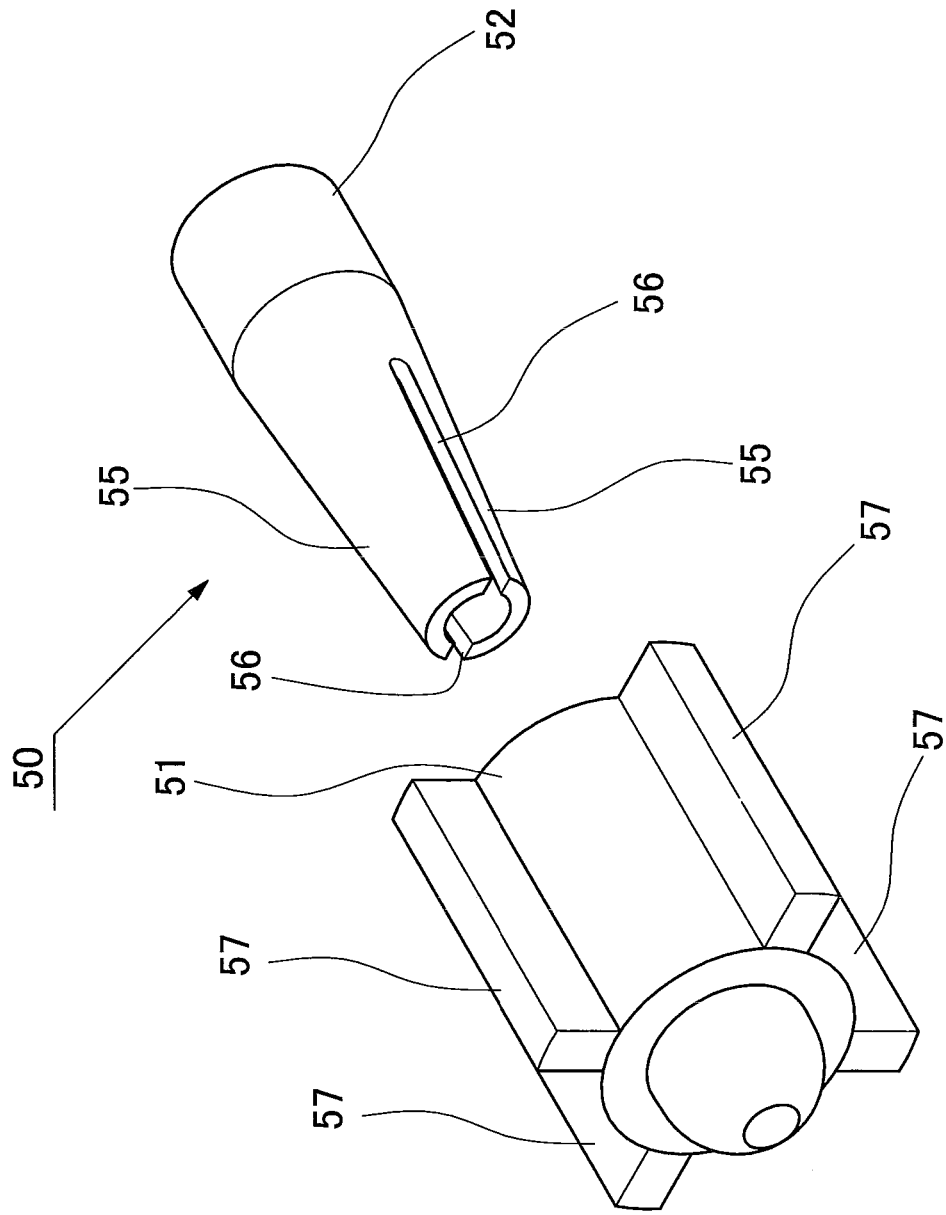
FIG. 9 is a schematic perspective view of the outer shell and the inner clamp tube.

As clearly seen in FIG. 9, the tubular outer shell 51 is provided with a body which is a far larger in outside diameter as compared with the narrow flexible cord 3, along with a number of grip protuberances 57 on and around its circumference, say, at intervals of 90 degrees, to ensure that tubular outer shell 51 is securely and stably gripped by operator's fingers at the time of adjusting the radial direction of the grasper assembly 2 of the forceps 1. That is to say, the tubular outer shell 51 can be turned about its axis smoothly and easily with fingers which are put on the longitudinal grip protuberances 57, along with the flexible sleeve 19 of the flexible cord 3 to turn the grasper assembly 2 of the forceps 1 to a radial direction facing toward a target point.

As shown in FIG. 4, the forceps 1 of the above-described construction is placed in the tool guide channel 45 through the tool entrance way 44 on the endoscope 40 and projected out of the tool exit opening 46 to perform a certain function or functions for a medical necessary treatment. In the case of the particular embodiment shown, the forceps 1 is a grasper type forceps which is adapted to grasp a lesion between a pair of grasping jaw members 10. However, when projected out of the tool exit opening 46, the grasping jaw members 20 of the grasper assembly 2 are not necessarily located in face to face relation with a lesion which requires a treatment. If not, the radial position of the forceps 1 is adjusted by turning the grasper jaw assembly 2 clockwise or counterclockwise through a certain angle until it comes face to face with a target lesion, while watching relative positions of the grasper assembly 2 and the target lesion in the view field of optical observation means 47 of the endoscope 40.

The radial position of the grasper assembly 2 which is projected out of the tool exit opening 46 is adjusted by the rotary tool adjustor 50 which is fixed on the flexible cord 3 at a position in the vicinity of the tool entrance way 44. Since the position of the rotary tool adjustor 50 on the flexible cord 3 is adjustable in the longitudinal direction, it can be located at a suitable position where it can be easily handled by an operator. A rotational force which is applied to the flexible cord 3 through the rotary tool adjustor 50 is transmitted securely to the fore distal end of the flexible cord 3 which is confined in the tool guide channel 45 in a restrained state. However, if the rotary tool adjustor 50 were located at a position remote from the tool entrance way 44, smooth and secure transmission of a rotational force would become difficult due to flexures of a lengthy cord portion intervening between the tool entrance way 44 and the rotary tool adjustor 50.

Thus, in order to transmit a rotational force of the rotary tool adjustor 50 securely from a flexible cord portion outside the tool entrance way 44 toward flexible cord portions within the tool guide channel 45, the rotary tool adjustor 50 should be located at a position immediately outside the tool entrance way 44 and at a position which is easily accessible by an operator for an adjustment of the position of the forceps 1 in radial direction. In this regard, in order to permit axial adjustments of the forceps 1 which is projected out of the tool exit opening 46, it is desirable to locate the rotary tool adjustor 50 at a distance of 2 to 5 cm from a concave recess 48a on the plug member 48 as shown in FIG. 6. However, the rotary tool adjustor 50 may be fixed in abutting relation with the concave recess 48a in a case where there is no need for axial adjustments of the position of grasping jaw members 10 of the forceps 1.

At the time of manipulating the rotary tool adjustor 50, an operator can easily hold up between his or her fingers the tubular outer shell 51 which is far larger in outside diameter than the flexible cord 3 and provided with four grip protuberances 57 at intervals around its circumference. Thus, the rotary tool adjustor 50 can be turned smoothly by operator's fingers in hold of the longitudinal grip protuberances 57 free of slippage. The rotary tool adjustor 50 is frictionally engaged with the sleeve 19 of the flexible cord 3, so that the flexible cord 3 is turned around its longitudinal axis in step with rotation of the rotary tool adjustor 50 to transmit the rotation to the grasper assembly 2 at the fore distal end of the flexible cord 3. In this manner, the grasper assembly 2 of the forceps 1 can be turned through a desired angle clockwise or counterclockwise to bring the same to an appropriately oriented radial position confronting a lesion to be grasped by the forceps 1. In this state, the manipulation handle 4 is pulled back and forth to open and close the grasping jaw members 10 for gripping a lesion securely therebetween.

In this instance, the grasping jaw members 10 are opened and closed by pulling back and force the manipulation wire 21 which is threaded internally of the sleeve 19 of the flexible cord 3, so that a loose flexible cord portion outside the tool entrance way 44 can be gripped in loops without affecting the pushing and pulling actions on the manipulation wire 21 in any way whatsoever. When the flexible cord 3 is gripped in loops outside the tool entrance way 44, the forceps 1 can be manipulated with higher maneuverability, particularly in turning the rotary tool adjustor 50 which is located in the vicinity of the tool entrance way 44 on the head grip 40 and in sliding the manipulation handle 4 back and force along the shank portion 30 for pushing and pulling the wire 21.

Figure 10:
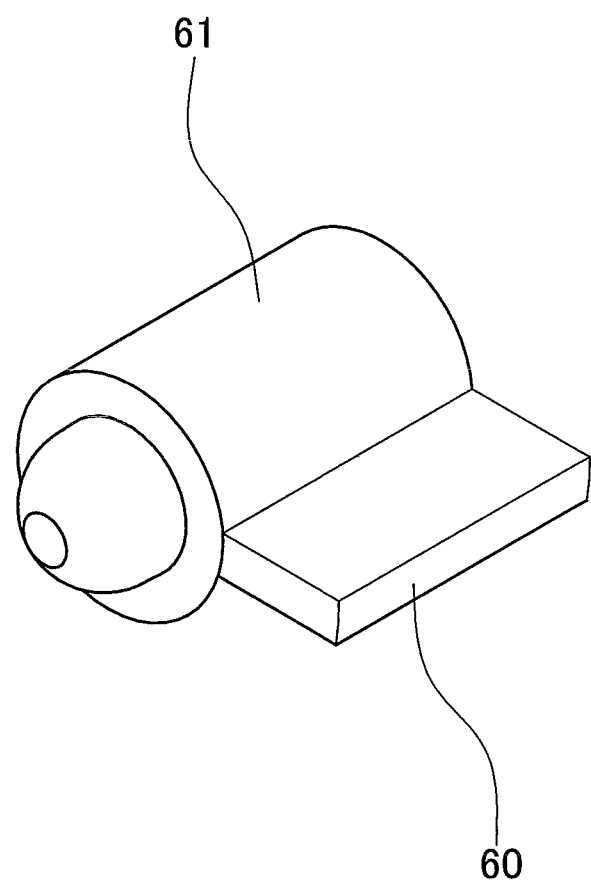
FIG. 10 is a schematic perspective view of an outer shell and an inner clamp tube of a rotary tool adjustor in a first modification according to the invention.
Figure 11:
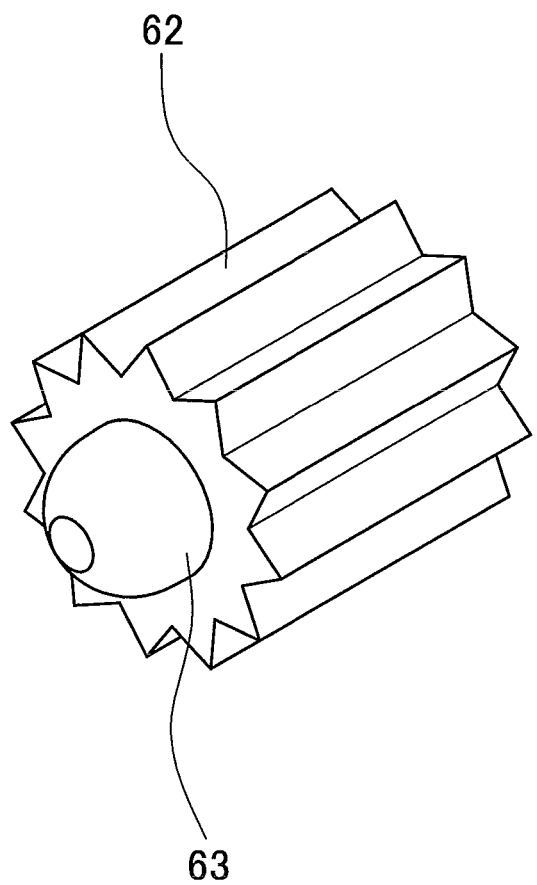
FIG. 11 is a schematic perspective view of an outer shell and an inner clamp tube of a rotary tool adjustor in a second modification according to the invention.
Figure 12:
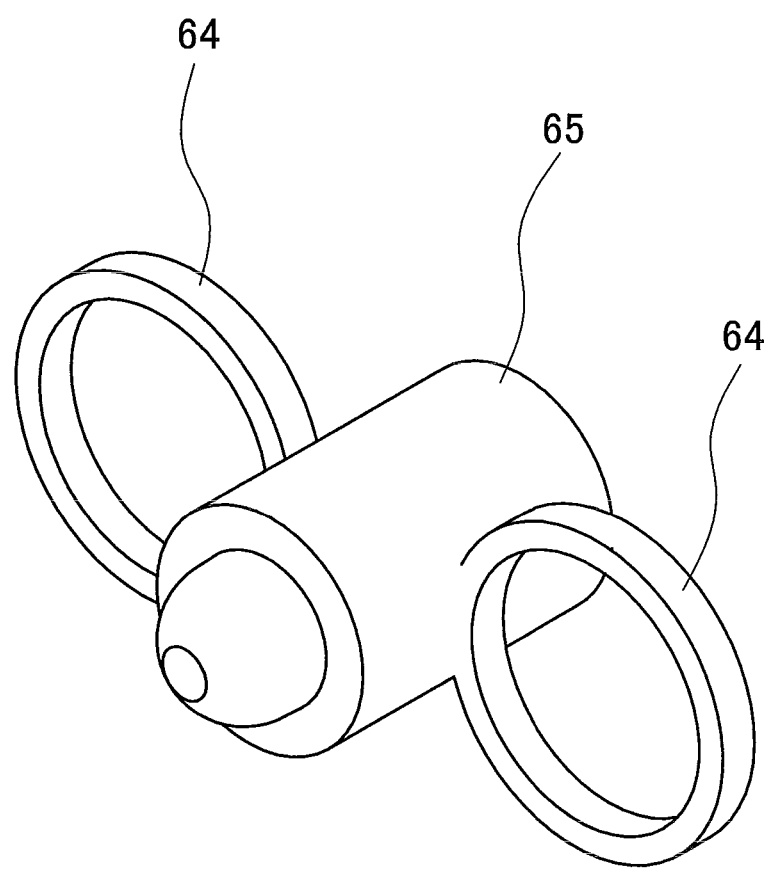
FIG. 12 is a schematic perspective view of an outer shell and an inner clamp tube of a rotary tool adjustor in a third modification according to the invention.
Figure 13:
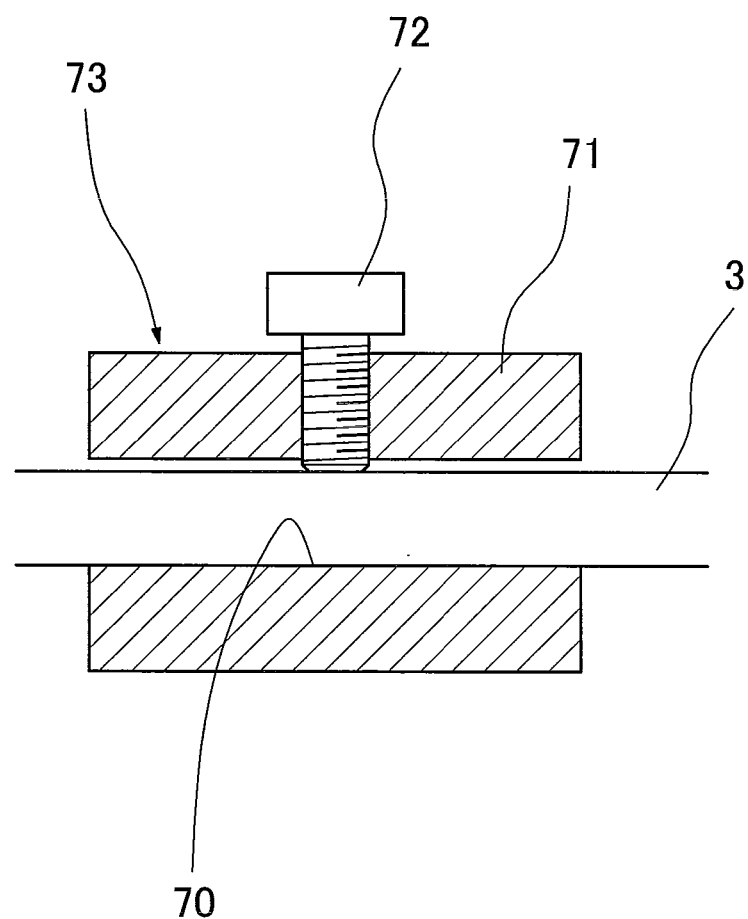
FIG. 13 is a sectional view, showing another modification of the rotational manipulation member.

Instead of the longitudinal grip protuberances 57 as described above, for example, a lever 60 may be provided on an outer shell 61 of the rotary tool adjustor to serve as a grip portion as shown in FIG. 10, or anti-slippage ridges 62 may be formed around the girder of an outer shell 63 of a rotary adjustor in the fashion of gear teeth as shown in FIG. 11. Further, a couple of finger hook rings 64 may be provided on the outer periphery of an outer shell 65 of a rotary adjustor as shown in FIG. 12. Alternatively, there may be employed a rotary tool adjustor 73 which is constituted by a tubular shell member 71 through which a flexible cord 3 is passed, and an anti-rotational stopper screw 72 which is radially threaded into the shell member 71 in such a way as to stop relative rotations of the flexible cord 3. If desired, the tubular outer shell 71 may be formed with the grip protuberances 57 of FIG. 9, lever 60 of FIG. 10, anti-slippage ridges 62 of FIG. 11 or finger holder hooks 64 of FIG. 12 integrally on its outer periphery. In a case where there is no necessity for adjusting the position of the rotary tool adjustor in the axial direction of the flexible cord, the rotary tool adjustor may be fixed in a predetermined axial direction by the use of an adhesive.

The invention claimed is:

1. An endoscopically inserting surgical tool having a tool action mechanism of said tool mounted at a distal end of a flexible cord to be placed in a tool guide channel of an endoscope through a tool entrance way on a manipulating head grip of said endoscope and projected out of a tool exit opening at a distal end of said tool guide channel, said tool action mechanism being actuated by way of a manipulation handle fixedly connected to a proximal end portion of said flexible cord, characterized in that:

said flexible cord has a length such that a proximal end portion thereof remains outside and rearward of said tool entrance way to said tool guide channel when a fore distal end portion is projected out of said tool exit opening of said tool guide channel over a necessary length for performing a required function;

said flexible cord being gripped in a rotary tool adjustor constituting an independent member from said manipulation handle, being provided in a position between said tool entrance way and said manipulation handle, apart from a connecting portion of said manipulation handle, on said manipulating head grip of said endoscope to turn said flexible cord clockwise or counterclockwise within said tool guide channel to adjust said action mechanism of said tool into an aimed radial direction; and said rotary tool adjustor is composed of a tubular outer shell internally defining a cord threading bore axially from rear to fore end thereof, and a clamp tube having a plural number of split clamp fingers to be brought into and out of frictional engagement with said flexible cord, said cord threading bore in said outer shell being tapered in such a way as to have a gradually reduced diameter toward said fore end, and said clamp tube having a tapered outer configuration in conformity with said cord threading bore of said outer shell;

whereby said rotary tool adjustor is adjustable in a longitudinal direction of said flexible cord toward or away from said tool entrance way;

wherein said proximal end portion of said flexible cord is led out of said tool entrance way through a plug member detachably fitted in at an outer end of said entrance way, and said rotary tool adjustor is rotatably set in position immediately on the outer side of said plug member;

wherein said flexible cord includes a tubular flexible sleeve one end of which is fixed to a proximal end of said tool action mechanism and which extends to a distal end of said manipulation handle, and a tool manipulation wire slidably inserted into said flexible tube, wherein said manipulation handle includes a slider for fixing a proximal end of said tool manipulation wire and sliding said tool manipulation wire, and a shank portion to which said flexible cord is fixed and which has a slit formed in an axial direction, and wherein said slider is disposed slidably along said slit of said shank portion and said tool manipulation wire is slid by sliding said slider to actuate said total action mechanism.

2. An endoscopically inserting surgical tool as set forth in claim 1, wherein said clamp fingers are each formed in an arcuate shape substantially in conformity in curvature with outside diameter of said flexible cord.

3. An endoscopically inserting surgical tool as set forth in claim 1, wherein said outer shell of said rotary tool adjustor is provided with projecting grip surfaces on outer peripheral side.

4. An endoscopically inserting surgical tool as set forth in claim 1, wherein said tool action mechanism is of a forceps including a pair of pivotally supported grasper members.

\* \* \* \* \*